United States Patent
Kennedy et al.

(10) Patent No.: US 7,337,673 B2
(45) Date of Patent: Mar. 4, 2008

(54) ULTRASONIC ARRAY PROBE APPARATUS, SYSTEM, AND METHOD FOR TRAVELING OVER HOLES AND OFF EDGES OF A STRUCTURE

(75) Inventors: James C. Kennedy, Renton, WA (US); Mark L. Little, Auburn, WA (US); Clyde T. Uyehara, Kent, WA (US)

(73) Assignee: The Boeing Company, Chicago, IL (US)

( * ) Notice: Subject to any disclaimer, the term of this patent is extended or adjusted under 35 U.S.C. 154(b) by 393 days.

(21) Appl. No.: 11/178,637

(22) Filed: Jul. 11, 2005

(65) Prior Publication Data

US 2007/0006657 A1    Jan. 11, 2007

(51) Int. Cl.
G01N 29/265    (2006.01)
G01N 29/28    (2006.01)

(52) U.S. Cl. .......................................... 73/633
(58) Field of Classification Search ................ 73/633, 73/634, 620, 619
See application file for complete search history.

(56) References Cited

U.S. PATENT DOCUMENTS

| | | | |
|---|---|---|---|
| 3,575,042 A * | 4/1971 | Lovelace et al. | 73/613 |
| 4,368,644 A * | 1/1983 | Wentzell et al. | 73/634 |
| 4,559,825 A * | 12/1985 | Martens | 73/622 |
| 5,062,301 A * | 11/1991 | Aleshin et al. | 73/629 |
| 5,786,535 A * | 7/1998 | Takeuchi et al. | 73/624 |
| 6,220,099 B1 * | 4/2001 | Marti et al. | 73/633 |
| 6,722,202 B1 | 4/2004 | Kennedy et al. | |
| 7,231,826 B2 * | 6/2007 | Bossi et al. | 73/618 |

OTHER PUBLICATIONS

U.S. Appl. No. 10/943,088, filed Sep. 16, 2004; In re: Georgeson et al.; entitled *Magnetically Attracted Inspecting Apparatus and Method Using a Ball Bearing*.
U.S. Appl. No. 10/943,135, filed Sep. 16, 2004; In re: Georgeson et al.; entitled *Magnetically Attracted Inspecting Apparatus and Method Using a Fluid Bearing*.

* cited by examiner

*Primary Examiner*—Hezron Williams
*Assistant Examiner*—Rose M Miller
(74) *Attorney, Agent, or Firm*—Alston & Bird LLP

(57) ABSTRACT

Improved apparatus, systems, and methods for inspecting a structure are provided that use a probe with sled appendages and an axial braking system. The probe uses pulse echo ultrasonic signals to inspect the structure. The sled appendages permit the probe to contact and ride along the surface of the structure and are rotatably connected and curved away from the surface of the structure to compensate for contoured surfaces and inspection around holes and edges. The axial braking system, in coordination with a motion control system moving the probe, fixes the positions of the sled appendages just before the probe travels over a hole or off an edge of the structure to prevent the probe from falling through the hole or off an edge and to permit the probe to return to the surface of the structure to continue inspection of the structure.

26 Claims, 4 Drawing Sheets

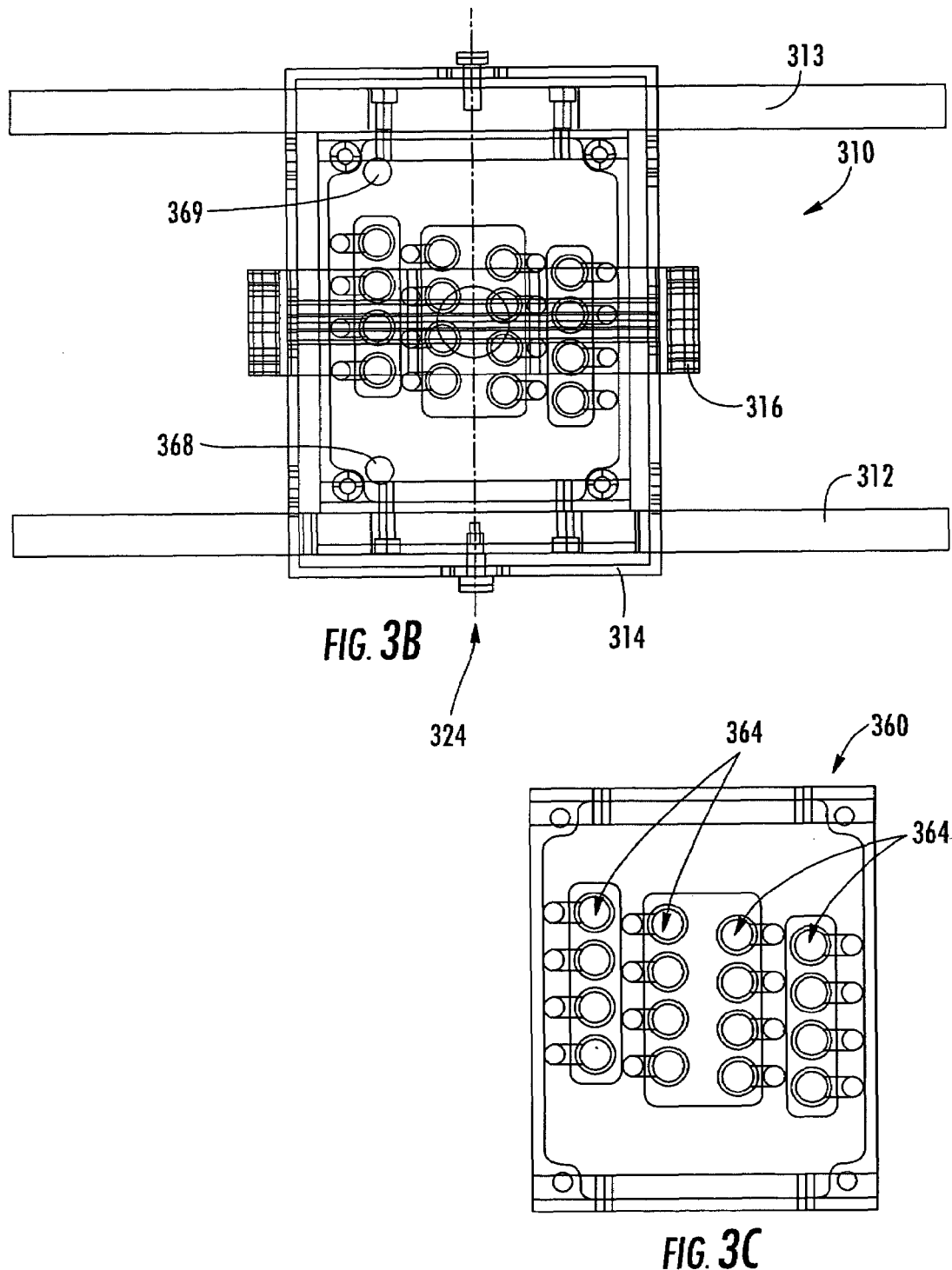

ULTRASONIC ARRAY PROBE APPARATUS, SYSTEM, AND METHOD FOR TRAVELING OVER HOLES AND OFF EDGES OF A STRUCTURE

CROSS-REFERENCE TO RELATED APPLICATIONS

The contents of U.S. Pat. Nos. 6,722,202; 7,231,826; application Ser. No. 10/943,088, entitled "Magnetically Attracted Inspecting Apparatus and Method Using a Ball Bearing," filed Sep. 16, 2004; application Ser. No. 10/943,135, entitled "Magnetically Attracted Inspecting Apparatus and Method Using a Fluid Bearing," filed Sep. 16, 2004; and application Ser. No. 11/178,584, entitled "Ultrasonic Inspection Apparatus, System, and Method," filed Jul. 11, 2005, are incorporated by reference.

FIELD OF THE INVENTION

The present invention relates generally to an apparatus, system, and method for inspecting a structure and, more particularly, to an apparatus, system, and method for non-destructive pulse echo ultrasonic inspection of a structure and inspection near holes and edges of the structure.

BACKGROUND

Non-destructive inspection (NDI) of structures involves thoroughly examining a structure without harming the structure or requiring its significant disassembly. Non-destructive inspection is typically preferred to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly used in the aircraft industry to inspect aircraft structures for any type of internal or external damage to or defects (flaws) in the structure. Inspection may be performed during manufacturing or after the completed structure has been put into service, including field testing, to validate the integrity and fitness of the structure. In the field, access to interior surfaces of the structure is often restricted, requiring disassembly of the structure, introducing additional time and labor.

Among the structures that are routinely non-destructively tested are composite structures, such as composite sandwich structures and other adhesive bonded panels and assemblies and structures with contoured surfaces. These composite structures, and a shift toward lightweight composite and bonded materials such as using graphite materials, dictate that devices and processes are available to ensure structural integrity, production quality, and life-cycle support for safe and reliable use. As such, it is frequently desirable to inspect structures to identify any defects, such as cracks, discontinuities, voids, or porosity, which could adversely affect the performance of the structure. For example, typical defects in composite sandwich structures, generally made of one or more layers of lightweight honeycomb or foam core material with composite or metal skins bonded to each side of the core, include disbonds which occur at the interfaces between the core and the skin or between the core and a buried septum.

Various types of sensors may be used to perform non-destructive inspection. One or more sensors may move over the portion of the structure to be examined, and receive data regarding the structure. For example, a pulse-echo (PE), through transmission (TT), or shear wave sensor may be used to obtain ultrasonic data, such as for thickness gauging, detection of laminar defects and porosity, and/or crack detection in the structure. Resonance, pulse echo or mechanical impedance sensors are typically used to provide indications of voids or porosity, such as in adhesive bondlines of the structure. High resolution inspection of aircraft structure is commonly performed using semi-automated ultrasonic testing (UT) to provide a plan view image of the part or structure under inspection. While solid laminates and some composite structures are commonly inspected using one-sided pulse echo ultrasonic (PEU) testing, composite sandwich structures are commonly inspected using through-transmission ultrasonic (TTU) testing for high resolution inspection. In through-transmission ultrasonic inspection, ultrasonic sensors such as transducers, or a transducer and a receiver sensor, are positioned facing the other but contacting opposite sides of the structure. An ultrasonic signal is transmitted by at least one transducer, propagated through the structure, and received by the other transducer. Data acquired by sensors is typically processed and then presented to a user via a display as a graph of amplitude of the received signal. To increase the rate at which the inspection of a structure is conducted, a scanning system may include arrays of inspection sensors, i.e., arrays of transmitters and/or detectors. As such, the inspection of the structure can proceed more rapidly and efficiently, thereby reducing the costs associated with the inspection. However, it has traditionally not always been possible to perform continuous scanning of a structure with holes and off the edges of the structure. For example, inspection probes which contact and ride along the surface of the structure under inspection and are typically supported against the structure by the pull of gravity or by pressure exerted by a motion control system, referred to as part-riding probes, may fall through a hole in a structure or off the edge of the structure. Although a structure can be inspected in a manner to scan around holes, a second inspection method typically must be performed for inspecting the edges of the structure and edges defining holes in the structure. For example, a technician can manually scan around the edges of the structure and the edges of holes in a structure using a pulse-echo or through transmission ultrasonic hand probe.

Non-destructive inspection may be performed manually by technicians who typically move an appropriate sensor over the structure. Manual scanning requires a trained technician to move the sensor over all portions of the structure needing inspection. While manual scanning may be required around the edges of the structure and the edges of holes in a structure, manual scanning may also be employed for scanning the remainder of the structure.

Semi-automated inspection systems have been developed to overcome some of the shortcomings with manual inspection techniques. For example, the Mobile Automated Scanner (MAUS®) system is a mobile scanning system that generally employs a fixed frame and one or more automated scanning heads typically adapted for ultrasonic inspection. A MAUS system may be used with pulse-echo, shear wave, and through-transmission sensors. The fixed frame may be attached to a surface of a structure to be inspected by vacuum suction cups, magnets, or like affixation methods. Smaller MAUS systems may be portable units manually moved over the surface of a structure by a technician. However, for through-transmission ultrasonic inspection, a semi-automated inspection system requires access to both sides or surfaces of a structure which, at least in some circumstances, will be problematic, if not impossible, particularly for semi-automated systems that use a fixed frame for control of automated scan heads.

Automated inspection systems have also been developed to overcome the myriad of shortcomings with manual inspection techniques. For single sided inspection methods, such as pulse echo ultrasonic inspection, a single-arm robotic device, such as an R-2000iA™ series six-axis robot from FANUC Robotics of Rochester Hills, Mich., or an IRB 6600 robot from ABB Ltd. of Zurich, Switzerland, may be used to position and move a pulse echo ultrasonic inspection device. For through transmission inspection, a device such as the Automated Ultrasonic Scanning System (AUSS®) system may be used. The AUSS system has two robotically controlled probe arms that can be positioned proximate the opposed surfaces of the structure undergoing inspection with one probe arm moving an ultrasonic transmitter along one surface of the structure, and the other probe arm correspondingly moving an ultrasonic receiver along the opposed surface of the structure. Conventional automated scanning systems, such as the AUSS-X system, therefore require access to both sides or surfaces of a structure for through transmission inspection which, at least in some circumstances, will be problematic, if not impossible, particularly for very large or small structures. To maintain the transmitter and receiver in proper alignment and spacing with one another and with the structure undergoing inspection, the AUSS-X system has a complex positioning system that provides motion control in ten axes. The AUSS system can also perform pulse echo inspections, and simultaneous dual frequency inspections.

Many structures, however, incorporate holes through which a part-riding probe may fall through and edges over which a part-riding probe may fall off. Further, most structures require inspection of edges around the structure and defining holes in the structure. Accordingly, improved apparatus, systems, and methods for inspecting structures with holes and inspecting structures at edges are desired.

SUMMARY OF THE INVENTION

The present invention provides an improved apparatus, systems, and methods for inspecting a structure using an inspection probe that includes sled-like appendages, referred to herein as sled appendages or sleds, an axial braking system and a probe extension braking system. Inspection probes according to the present invention may be used in conjunction with a motion control system that both moves the probe over the structure for inspection and operates with the axial and extension braking systems for when the probe travels over holes or off edges of the structure. An inspection probe may also be used with an extension coupling device between the motion control system and the probe to press the probe against the structure for adjusting to changes in surface contours of the structure, rather than requiring the motion control system to make detailed changes in orientation and movement of the probe to adjust to changes in surface contours. Either the motion control system or a separate device, such as an extension coupling device, would be used to press the inspection probe against the structure so the inspection probe will ride across the structure on the sled appendages. Embodiments of the present invention combine the physical structure of the sled appendages with the axial braking system to fix the position of the sled appendages for traveling over holes or off an edge of the structure, including large holes or cut-outs in the structure which are also referred to herein as holes. Embodiments of the present invention can be used for various inspection applications but are particularly useful for inspection of structures that include holes and require inspection of the edges around the structure or defining a hole or have contoured surfaces. A probe will include one or more sensors, typically pulse echo ultrasonic transducers, possibly defining an array of pulse echo ultrasonic transducers. Such devices can be used for high resolution defect detection in structures of varying shapes and sizes. Embodiments of apparatus, systems, and methods of the present invention can be used for inspection of structures during manufacture or in-service. Further, embodiments of the present invention provide new inspection capabilities for non-destructive inspection of large and small structures, particularly including the edges of structures and structures with holes.

Embodiments of apparatus, systems, and methods of the present invention typically operate in array modes using an array of pulse echo ultrasonic transducers, thereby increasing inspection speed and efficiency while reducing cost. Apparatus, systems, and methods of the present invention are also capable of operating with a single or a plurality of pulse echo ultrasonic transducers.

For continuous scanning applications, embodiments of apparatus, systems, and methods of the present invention permit the probe to contact and ride along the surface of the structure using one or more sled appendages, thereby reducing the necessary sophistication of a motion control system that is typically required by conventional scanning systems to maintain the probe in a predefined orientation and predefined position with respect to the surface of the structure. By allowing the probe to ride across the structure, the motion control system, or a separate device such as an extension coupler, only needs to press the probe against the structure, but does not need to know the surface contours of the structure because the act of pressing the probe against the surface combined with the sled appendages having freedom of motion and the axial motion of the probe compensate for surface contours. In addition to sled appendages, the probe may also use contact members to support the probes against the respective surfaces of the structure, such as roller bearings along the bottom of the sled appendages. The sled appendages are rotatably connected to permit freedom of motion of the sled appendages for riding along contoured surfaces. Contact with the surface ensures consistent orientation of transducers with respect to the structure for pulse echo ultrasonic inspection. Contact with the surface also permits accurate position measurement of the inspection device during continuous scanning, such as keeping an optical or positional encoder in physical and/or visual contact with the surface of the structure under inspection. Contact with the surface also permits the probe to disperse a couplant between the surface of the structure and the pulse echo ultrasonic transducers. Where a couplant is used, a probe may also include a bubbler shoe that disperses the couplant around each pulse echo ultrasonic transducer to independently couple the signal from each transducer to the surface of the part. By individually coupling each transducer to the surface of the part, the bubbler shoe compensates for when the probe travels over a hole or off an edge of the structure where all of the transducers are not over the surface of the structure. In such a manner, only the probes over the hole or off the edge of the structure will lose the coupling with the surface, but the transducers remaining over the surface of the structure will continue to be independently coupled.

The axial and extension braking systems of a probe are used to fix the position of the sled appendages for traveling over holes or off an edge of the structure. Thus, for continuous scanning applications, the probe contacts and rides along the surface of the structure on the sled appendages, but as the probe approaches a hole or edge, the axial and extension braking systems, either using data of the hole and edge positions for the structure and the current location of the probe or using braking signals from a motion control system, fixes the current position of the sled appendages for traveling over the hole or off an edge and again contacting and riding along the surface of the structure after passing the hole or retracting from the edge at which time the axial braking system releases to permit the sled appendages to follow the contour of the surface of the structure. An axial braking system of an embodiment of a probe of the present invention can operate in more than one axis, and typically operates in two perpendicular axes referred to herein as the x-axis perpendicular to the distal length of the sled appendages to control the front-to-back tilt, or pitch, of the sled appendages and the y-axis parallel to the distal length of the sled appendages to control the side-to-side slant, or roll, of the sled appendages.

According to one aspect of the present invention, an apparatus, system, and method for non-destructive inspection of a structure includes a probe which is configured for traveling over a surface of the structure along sled appendages and using an axial braking system for traveling over holes and off edges of the structure. The probe includes at least one pulse echo ultrasonic transducer. A plurality of pulse echo ultrasonic transducers may be arranged in an array for faster and more complete scanning of the structure. If a couplant is used to couple the transducers to the surface of the structure, the probe may include a bubbler shoe to individually couple each transducer to the surface of the structure to prevent loss of coupling of transducers remaining over the surface of the structure when one or more transducers are over a hole or off an edge. The probe may also include a visual inspection sensor for providing position or optical information related to the location of the probe or transducers thereof.

According to another aspect of the present invention, a method may include providing a probe with at least one pulse echo ultrasonic transducer, at least one sled appendage for contacting a surface of a structure, and axial and extension braking systems; transmitting pulse echo ultrasonic signals from the transducer into the structure; receiving pulse echo ultrasonic signals at the transducer from the structure; and fixing the position of the sled for scanning a portion of the structure where only a portion of the probe is over the surface of the structure.

BRIEF DESCRIPTION OF THE DRAWING(S)

FIG. 3B is a top plan view of the inspection apparatus of FIG. 3A.

FIG. 3C is a top plan view of the bubbler shoe of the inspection apparatus of FIG. 3A.

DETAILED DESCRIPTION

Figure 1:
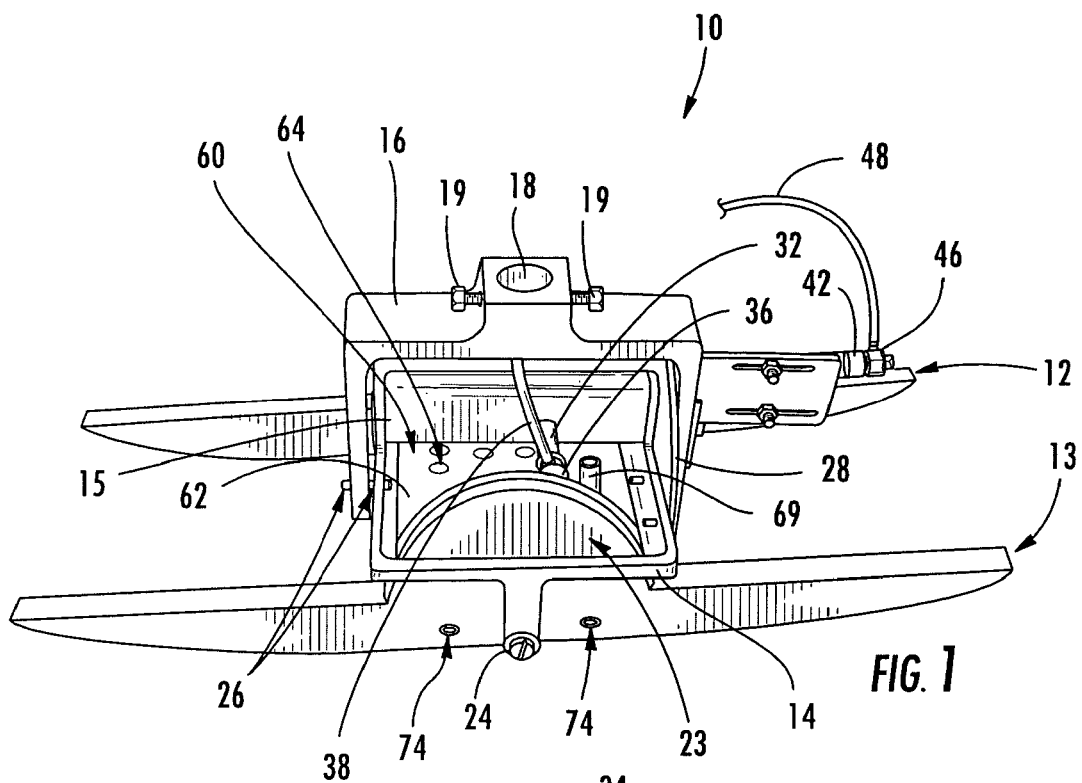
FIG. 1 is a schematic diagram of an embodiment of an inspection apparatus of the present invention.

The present invention will be described more fully with reference to the accompanying drawings. Some, but not all, embodiments of the invention are shown. The invention may be embodied in many different forms and should not be construed as limited to the described embodiments. Like numbers and variables refer to like elements and parameters throughout the drawings.

The term "holes" refers to holes of varying sizes in a structure, including features described as "cut-outs" in the structure. The term "edges" refers generally to the sides of the structure, but also includes reference to the perimeter of holes, particularly large holes or cut-outs through which a conventional part-riding probe might fall through. Thus, holes may be described as having edges, and the term edges is inclusive of both an external perimeter of a structure and perimeters of internal holes in the structure. Although being characteristically different, for purposes of the present invention holes and edges differ primarily by the manner in which a probe of the present invention operates near these features. For example, the probe typically travels over a hole or cut-out but travels off an edge of the structure, and possibly returning over the structure from an edge. Further, while in some instances in the description below using only one of the two terms holes and edges may be sufficient, typically both terms are used to emphasize that the described function or operation applies to both holes in the structure and edges of the structure, and not merely one of these features.

The term "rotatably" refers to a characteristic of angular motion in at least one plane, and typically only one plane as may be defined by a connection about an axis-line as described in the examples below. However, a rotatable connection may also be defined by a connection that provides angular motion in more than one plane, such as a ball-and-socket joint connection that permits motion of the joint without permitting rotation in at least one plane, such as to provide freedom of motion to pitch and roll, but not yaw.

The present invention provides apparatus and methods for an ultrasonic array probe for inspecting a structure while riding on a surface of the structure. The probe has the ability to travel over holes and off edges of the structure during inspection. Typically a probe according to the present invention would be moved over a structure by a motion control system, such as an R-2000iA™ series six-axis robot from FANUC Robotics, an IRB6600 robot from ABB, or similar automated robotic motion control system, and possibly also using an extension coupler to compensate for surface contours rather than requiring the motion control system to compensate for surface contours. An example motion control system with an extension coupler for manipulating an inspection apparatus of the present invention is described in application Ser. No. 11/178,584, entitled "Ultrasonic Inspection Apparatus, System, and Method," which is incorporated by reference. The combination of sled appendages and an axial braking system provide the configuration for the probe to be able to travel over holes and off edges of the structure during inspection. By comparison, conventional part-riding probes, probes which contact and ride along the surface of the structure under inspection, may fall through a large hole or off the side of a part rather than having the ability to travel over holes and off the edge of a part for inspection. Using conventional part-riding probes, a structure typically is scanned in a manner to go around holes and to not inspect near edges, leaving the edges of the structure to be inspected by a second inspection method, such as by a technician using a manual pulse echo scanning device. Sled appendages, or sleds, of a probe according to the present invention are linear extensions rotatably attached to the bottom of the probe and upon which the probe rides over a surface of the structure. An axial braking system according to the present invention operates to temporarily fix the current positions of the sled appendages to maintain those positions while the probe travels over a hole or off an edge of the structure. An axial braking system may operate in one or more axes. For example, the braking system may lock simply in an x-axis, in both x- and y-axes, or in x-, y-, and z-axes. The axial braking system fixes the position of the sled appendages by locking the axes of motion of the sled appendages before traveling over a hole or off an edge of the structure.

Although in some instances the length of sled appendages may be sufficient to pass over a small hole without needing to use the axial braking system of the probe, the combination of sled appendages and axial braking system are generally provided and used for instances when the probe would otherwise fall through a large hole or off an edge of a structure like a conventional part-riding probe were it not for the operation of the axial braking system to maintain the position of the sled appendages while the probe moves over a hole or off an edge of the structure. Further, by using a probe according to the present invention, a motion control system does not need to maintain or know the precise shape or contour of the structure, but merely the location of holes and edges of the structure so the axial braking system can fix the position of the sled appendages before the probe is passed over a hole or off an edge of the part. Further, although the inspection apparatus described and depicted herein includes two sled appendages located on opposing sides of the inspection apparatus, and an inspection apparatus according to the present invention typically includes two sled appendages, an inspection apparatus of an embodiment of the present invention might include only a single sled appendage such as a sled appendage with a broad surface width for providing side-to-side balance to the inspection apparatus. Alternative embodiments of an inspection apparatus may include a plurality of sled appendages extending below the inspection apparatus and/or to the sides of the inspection apparatus.

A probe may also include a bubbler shoe. A bubbler shoe according to the present invention provides a couplant around each transducer for individually coupling each transducer of the probe that remain over the structure for inspection even when other transducers may be over holes or off an edge of the structure. By comparison, conventional coupling shoes typically provide a cavity that surrounds all of the transducers to act as a single couplant for all of the transducers. Thus, if a conventional probe travels over a large hole or off an edge of the part, the water cavity will empty and the ultrasonic signals of all of the transducers may be lost or will be degraded due to the lack of coupling between the structure and the transducers. However, when using a bubbler shoe of an embodiment of the present invention, only the transducers that are over the hole or off the edge of the structure may lose coupling for ultrasonic signals while the transducers remaining over the structure retain the coupling provided by the bubbler shoe.

Figure 2:
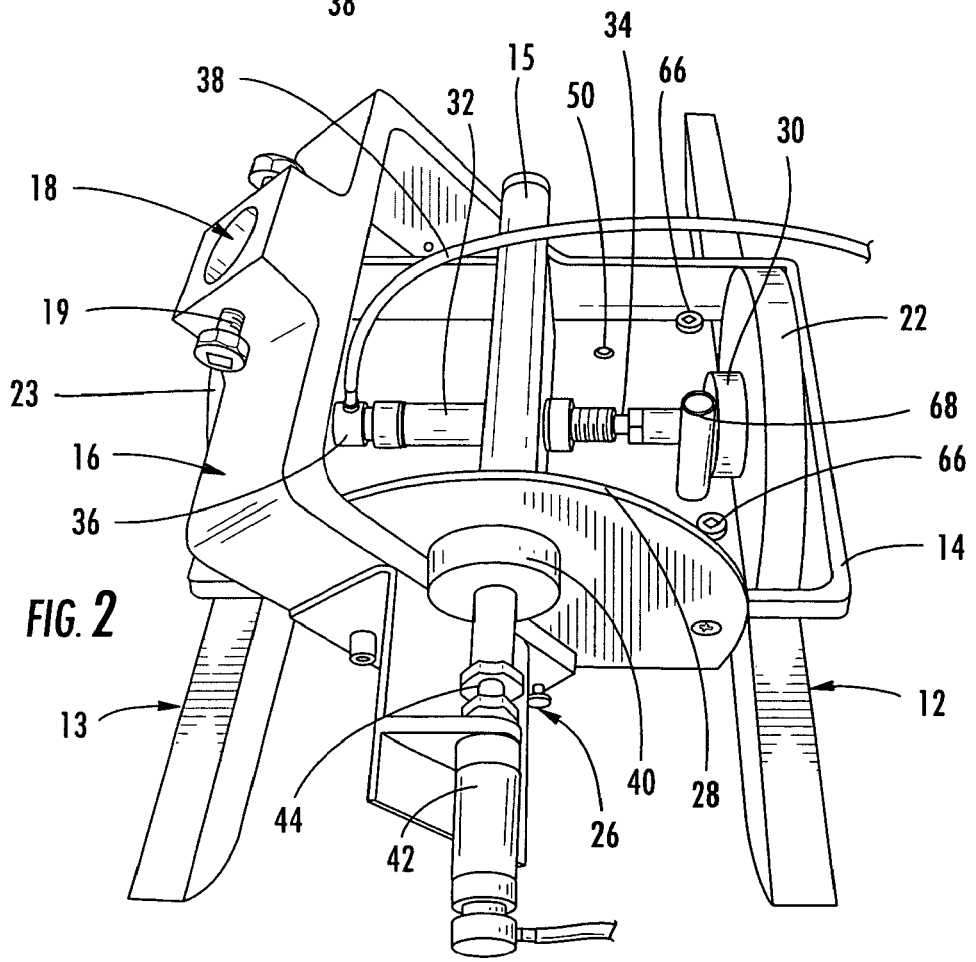
FIG. 2 is another view of the schematic diagram of the inspection apparatus of FIG. 1.

FIGS. 1 and 2 are schematic diagrams of an embodiment of an inspection apparatus according to the present invention, also generally referred to as a probe or inspection probe. The inspection apparatus 10 includes two sled appendages 12, 13 located on opposite sides of the inspection apparatus 10. The sled appendages 12, 13 are rotatably attached to a frame member 14 of the inspection apparatus 10 about a first axis 24 defining a first direction of motion for the sled appendages 12, 13, also referred to as an x-axis, front-to-back tilt axis, or pitch axis. The frame of the inspection apparatus 10 also includes a second frame member 16 which is rotatably connected to the first frame member 14 about a second axis 26 defining a second direction of motion for the sled appendages 12, 13, also referred to as a y-axis, side-to-side slant axis, or roll axis. By having two rotational axes, the sled appendages 12, 13 are capable of rotating in at least two directions of motion with respect to a motion control system connected to the inspection apparatus 10, such as by way of an attachment at the opening 18 and securing screws 19, to compensate for surface variations of the structure, such as shape and contour characteristics of the surface. Further, because as described below, a transducer holder or bubbler shoe for an inspection apparatus of the present invention is connected to sled appendages, rather than the frame, the transducers maintain the same position and orientation as achieved by the sled appendages, thereby providing the transducers a consistent orientation with respect to the surface of the structure over which the inspection apparatus rides on the sled appendages. Maintaining a consistent orientation, distance and angle, of the transducers with respect to the surface of the structure ensures consistent quality of inspection by the transducers.

At least one of the sled appendages 12, 13 includes an upper portion 22, 23 that functions as a stationary brake plate against which a brake disc 30 of the axial braking system can be applied to fix the position of the sled appendage about the first axis of motion 24. An axial braking system of an embodiment of the present invention may also include a pneumatic brake cylinder 32 with an extendable piston arm 34 to which a brake disc 30 is attached at the distal end of the extendable piston arm 34 protruding from the brake cylinder 32. A brake cylinder 32 may be activated by any conventional method, such as by compressing a fluid, typically air, through a supply line 38 into a valve 36 attached to the brake cylinder 32. When the brake mechanism is activated, the compression of fluid causes a piston inside the brake cylinder 32 and attached to the distal end of the extendable piston arm 34 inside the brake cylinder 32 to force the extendable piston arm 34 out of the brake cylinder 32 to force the brake disc 30 to press against the stationary brake plate 22, 23 of one or more sled appendages 12, 13.

To fix the position of the sled appendages in the second axis of motion 26, a second brake plate 28 may be affixed to the first frame member 14 to permit a second brake mechanism 40, 42, 44, 46, 48, to engage the second stationary brake plate 28 in the same manner that the first brake mechanism 30, 32, 34, 36, 38 engages the first stationary brake plate 22, 23 to fix the position of the sled appendages 12, 13 about the first axis of motion 24. The first frame member 14 may include a vertical support member 15 connected to the second stationary brake plate 28 to provide stability between the first frame member 14 and the second stationary brake plate 28, such as when a brake disc 40 is pressed against the second stationary brake plate 28 to fix the position of the sled appendages in the second axis of motion 26. An axial braking system of an alternative embodiment may also include a brake mechanism in a third direction of motion, such as a vertical z-axis with respect to the surface of the structure, and may be incorporated into an attachment to a motion control system.

To improve braking capabilities of a braking system, brake discs and/or stationary brake plates may be coated with or include an attached layer of material, such as being coated with rubber, to cause increased friction between a brake disc and stationary brake plate for fixing the positions of sled appendages and preventing slippage of the positions of the sled appendages.

The inspection apparatus 10 includes at least one pulse echo ultrasonic transducer 50. If not using a couplant between the transducers 50 of the inspection apparatus 10 and the structure, a transducer holder may be attached to the sled appendages 12, 13 to support the transducers 50, such as supported in an array where a plurality of transducers are used to increase the inspection coverage area. As mentioned above, by attaching the transducer holder, or bubbler shoe as described below, to the sled appendages 12, 13 the transducer holder and transducers 50 supported thereby also maintain constant orientation with the surface of the structure over which the inspection apparatus 10 rides because the inspection apparatus 10 rides over the surface of the structure on the sled appendages 12, 13. Because inspection of a structure typically requires ensuring that the transducers maintain constant orientation, distance and angle, with respect to the surface of the structure, attaching a transducer holder, or bubbler shoe, to sled appendages ensures that the transducer holder, or bubbler shoe, and transducers supported thereby also maintain constant orientation with respect to the surface of the structure for consistent quality of inspection by the transducers.

If a couplant is to be used to couple the ultrasonic signals from the transducers 50 into the structure and reflected from the structure back to the transducers 50, a bubbler shoe 60 may be incorporated into the inspection apparatus 10. The bubbler shoe 60 individually couples each transducer 50 rather than using a single cavity to couple all of the transducers 50. A bubbler shoe may include a top (or first) layer 62 that includes holes 64 to permit access to the transducers 50, such as by the transducer protruding through the holes 64 in the top layer 62 or by permitting a wired connection through the holes 64 in the top layer 62 for communication with the transducers 50. The top layer 62 may also include one or more fluid inlets 68, 69 through which a couplant may be injected into the bubbler shoe 60. The bubbler shoe 60 may also include a bottom (or second) layer that, together with the top layer 62, define a cavity through which a couplant from the fluid inlet 68, 69 can flow to individually couple each transducer 50. By way of example, such cavities may be a single open cavity providing a fluid path to each transducer or may be a cavity structured with a manifold configuration whereby the couplant passes into separate subcavities that lead to the individual transducers. The bottom layer includes holes through which the couplant passes to couple the transmission of ultrasonic signals from the transducers 50. The transducers 50 may pass through the holes in the bottom layer, may terminate inside the cavity, or may terminate within the bottom layer.

Figure 3A:
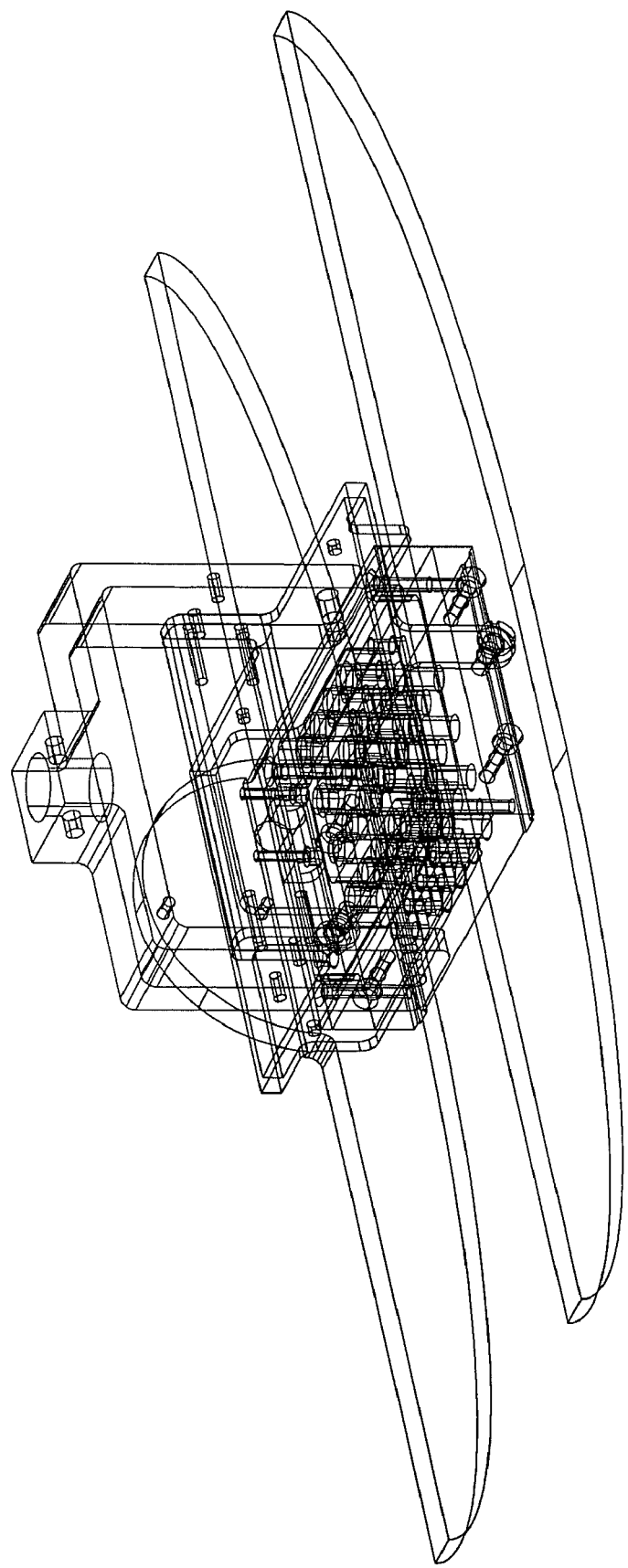
FIG. 3A is a schematic diagram of another embodiment of an inspection apparatus of the present invention.

FIG. 3A is a schematic diagram of another embodiment of an inspection apparatus of the present invention. FIG. 3B is a top plan view of the inspection apparatus of FIG. 3A. FIG. 3C is a top plan view of the bubbler shoe of the inspection apparatus of FIG. 3A. The inspection apparatus 310 of FIGS. 3A, 3B, and 3C differs from an inspection apparatus 10 of FIGS. 1 and 2 in that the inspection apparatus 310 of FIGS. 3A, 3B, and 3C provides only one axis of motion 324 for the sled appendages 312,313, while the inspection apparatus 10 of FIGS. 1 and 2 provides two axes of motion 24, 26 for the sled appendages 12, 13. Although a bubbler shoe 60 with a transducer array is present in the inspection apparatus 10 of FIGS. 1 and 2, FIGS. 3A, 3B, and 3C clearly show an example configuration for an array of transducers in the bubbler shoe 360 of the inspection apparatus 310. While the internal construction of the bubbler shoe 360 is visible to some extent in FIG. 3A, FIG. 4 clearly shows an example internal construction of another bubbler shoe 460.

Figure 4:
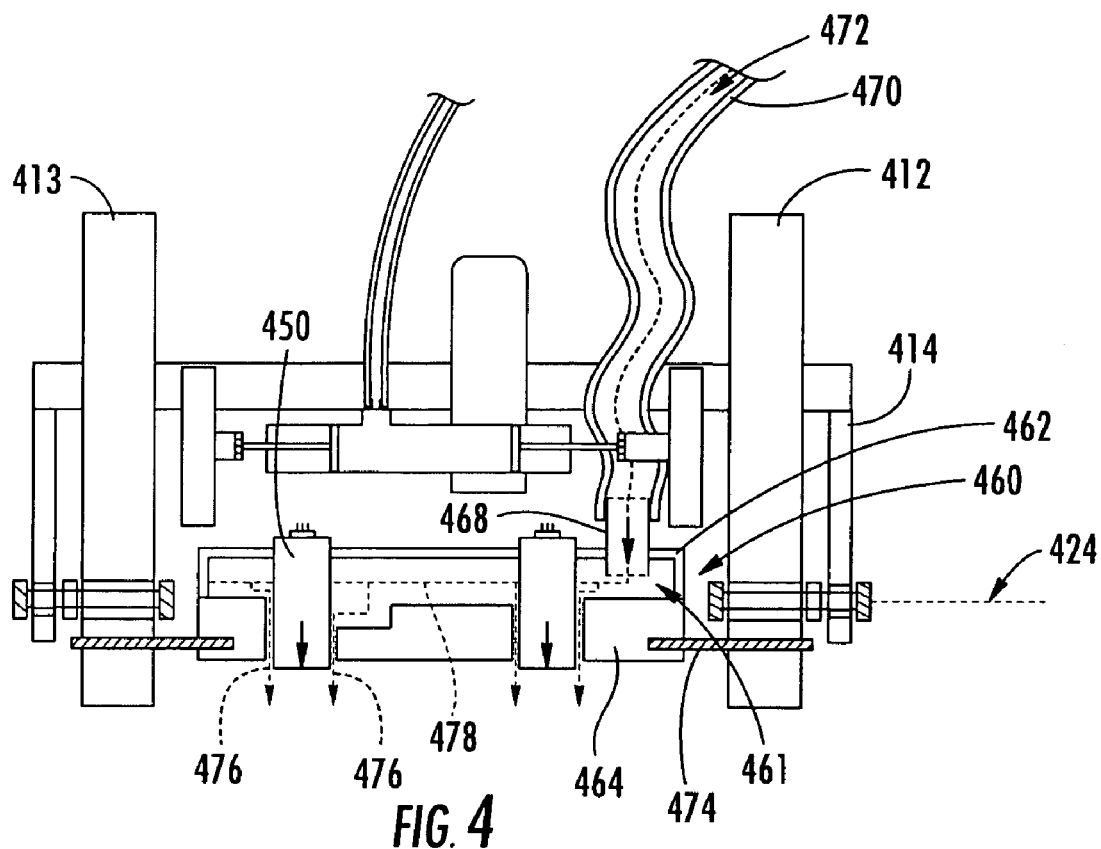
FIG. 4 is a cross-section of a schematic diagram of yet another embodiment of an inspection apparatus of the present invention.

FIG. 4 is a cross-section of a schematic diagram of yet another embodiment of an inspection apparatus of the present invention. The cross-section represents an approximate mid-point through a first axis of rotation 424 corresponding to the front-back tilt of the sled appendages 412, 413. The cross-sectional view shows the internal structure of one embodiment of a bubbler shoe 460 for individually coupling each transducer 450 according to the present invention. The bubbler shoe 460 includes a top layer 462 and a bottom layer 464 configured together to form a cavity 461 into which a couplant is injected for being dispersing about the cavity 461 and, after filling the cavity 461, being evenly dispersed around each of the transducers 450 to couple the ultrasonic signals from the transducers 450 to the structure. A fluid couplant path 472 passes through a supply line 470 into and through a fluid inlet 486 into the bubbler shoe 460. The couplant path continues to disperse throughout the cavity 461 as indicated by the fluid couplant path 478. The ejection of the couplant from the cavity 461 of the bubbler shoe 460 around each of the transducers 450 is indicated by fluid couplant paths 476. Typically water may be used for a couplant, but other fluids may be used, including a gas, such as air.

The cross-section of the inspection apparatus of FIG. 4 also shows how the bubbler shoe 460 may be connected to the sled appendages 412, 413 to maintain constant orientation with respect to the structure by the bubbler shoe 460 and transducers 450 supported thereby. The connection 474 between the sled appendages 412, 413 and the bottom layer 464 of the bubbler shoe 460 provides a non-rotational connection between the bubbler shoe 460 and the sled appendages 412, 413. By comparison to the first axis of motion 424, the connection 474 is not a rotational axis that provides a direction of motion but is fixed to provide the same orientation with respect to the structure that the sled appendages 412, 413 have to the bubbler shoe 460 and transducers 450 supported thereby.

Figure 5:
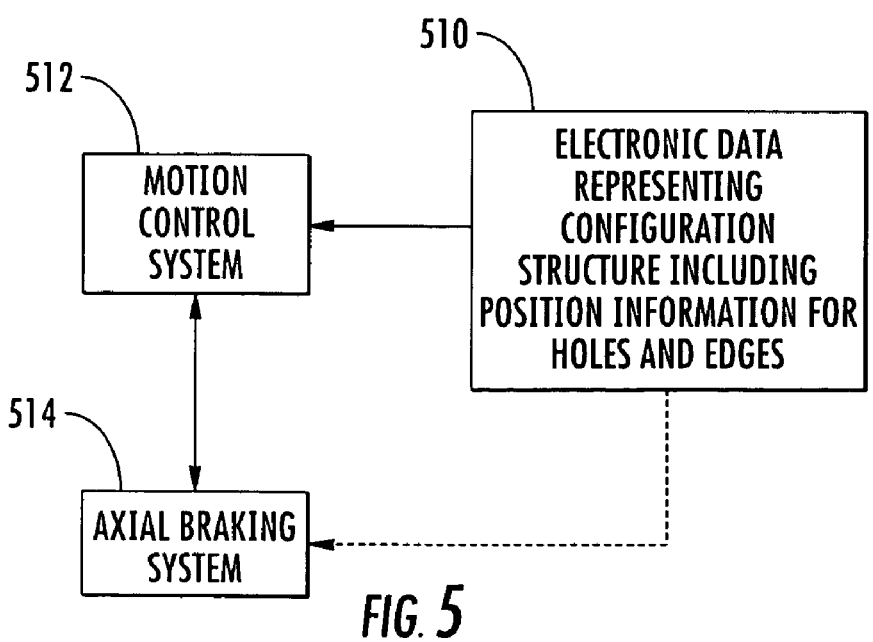
FIG. 5 is a block diagram of an embodiment of an inspection system of the present invention.

FIG. 5 is a block diagram of an inspection system of the present invention. The block diagram shows communication between a motion control system 512 and an axial braking system 514. In addition, electronic data 510 representing the configuration of the structure under inspection, including position information for holes in edges of the structure, is provided to the motion control system 512. An alternative embodiment for an inspection system may include an axial braking system that incorporates hardware and software to interpret the position of the inspection apparatus with respect to holes and edges of the structure, referred to as a smart axial braking system. For example, a smart axial braking system may include some form of a position encoder or positioning system that operates to identify the location of the inspection apparatus with respect to the structure and electronic data representing the configuration of the structure, such as the electronic data 510 provided to the motion control system in the embodiment shown in FIG. 5.

The axial braking system 514 may be activated based on data provided by the motion control system 512. For example, the motion control system 512 may incorporate software that interprets the position of the inspection apparatus with respect to holes in edges of the structure and indicate to the axial braking system 514 when to activate the braking mechanisms on an inspection apparatus to fix the positions of sled appendages on the inspection apparatus and when to deactivate the braking mechanisms. For example, when the motion control system 512 identifies that the inspection apparatus is about to travel over a hole, the motion control system 512 can communicate to the axial braking system 514 to fix the current position of the sled appendages for while the inspection apparatus travels over the hole. When the motion control system 512 determines that the inspection apparatus has passed over the hole, the motion control system 512 may communicate to the axial braking system 514 to release the sled appendages so they may continue to ride along and follow the contoured surface of the structure. For example, a solenoid actuated pneumatic switch of the axial braking system 514 may activate to apply pressure to a pneumatic brake cylinder to extend brake discs against stationary brake plates on the sled appendages. The activation of the solenoid actuated pneumatic switch may be controlled by output signals provided by the motion control system 512 to indicate to the axial braking system 514 to fix the positions of the sled appendages.

Alternatively, the motion control system 512 may provide location data of the inspection apparatus with respect to a structure being inspected to the axial braking system 514, and the axial braking system 514 may use the location data, in addition to electronic data 510 representing the configuration of the structure either provided through the motion control system 512 or directly to the axial braking system 514, to determine when the axial braking system 514 should activate braking mechanics on the inspection apparatus to fit the positions of sled appendages, such as before traveling over a hole or off an edge of the structure.

The invention should not be limited to the specific disclosed embodiments. Specific terms are used in a generic and descriptive sense only and not for purposes of limitation.

That which is claimed:

1. An apparatus for non-destructive inspection of a structure, comprising:
    at least one pulse echo ultrasonic transducer configured for inspecting the structure as the transducer is moved over the structure;
    a frame configured for supporting the transducer;
    at least one sled appendage configured for supporting the frame while traveling over a surface of the structure and rotatably connected to the frame; and
    a braking system capable of affixing the respective positions of the frame and sled appendage in at least a first direction of motion about a first axis defined by the rotatable connection of the frame and the sled appendage.

2. The apparatus of claim 1, wherein the braking system comprises:
    a stationary brake plate connected to the sled appendage;
    a brake cylinder connected to the frame and comprising an extendable piston; and
    a first brake disc mounted to a first distal end of the piston protruding from the brake cylinder,
    wherein the braking system is capable of affixing the respective positions of the frame and the sled appendage in the first direction of motion by the brake cylinder extending the extendable piston to push the first brake disc against the stationary brake plate.

3. The apparatus of claim 2, wherein at least one of the first brake disc and stationary brake plate comprises a rubber material affixed to at least one of a surface opposing the stationary brake plate and a surface opposing the brake disc, respectively.

4. The apparatus of claim 2, wherein the brake cylinder is a pneumatic brake cylinder.

5. The apparatus of claim 2, further comprising a pair of sled appendages configured to rotate independently in the first direction, wherein each sled appendage comprises a stationary brake plate, wherein the extendable piston comprises a second distal end protruding from an opposing end of the brake cylinder as the first distal end, wherein a second brake disc is mounted to the second distal end, and wherein the braking system is capable of affixing the respective positions of the frame and the sled appendages in the first direction by the brake cylinder extending the piston to push the first and second brake discs against the stationary brake plates of the sled appendages.

6. The apparatus of claim 2, further comprising:
    a pair of sled appendages configured to rotate independently in the first direction, wherein each sled appendage comprises a stationary brake plate;
    a secondary brake cylinder connected to the frame and comprising a extendable secondary piston; and
    a secondary brake disc mounted to the distal end of the secondary piston protruding from the secondary brake cylinder;
    wherein the braking system is capable of affixing the respective positions of the frame and the sled appendages in the first direction by the brake cylinder extending the piston of the brake cylinder to push the first brake disc against the stationary brake plate of one of the sled appendages and the secondary brake cylinder extending the secondary piston of the secondary brake cylinder to push the secondary brake disc against the stationary brake plate of the other sled appendage.

7. The apparatus of claim 1, wherein the frame comprises a first portion and a second portion, wherein the first portion is rotatably connected to the sled appendage and the second portion is rotatably connected to the first portion, and wherein the frame is further configured for providing a second direction of motion about a second axis different from the first axis and defined by the rotatable connection between the first and second portions of the frame, and wherein the braking system is further capable of affixing the respective positions of the first and second portions of the frame in the second direction about the second axis.

8. The apparatus of claim 7, wherein the braking system comprises:
    two stationary brake plates, a first stationary brake plate connected to the sled appendage and a second stationary brake plate connected to the first portion of the frame;
    two brake cylinders, a first brake cylinder connected to the first portion of the frame and comprising a first extendable piston and a second brake cylinder connected to the second portion of the frame and comprising a second extendable piston; and
    two brake discs, a first brake disc mounted to the distal end of the first extendable piston protruding from the first brake cylinder and a second brake disc mounted to the distal end of the second extendable piston protruding from the second brake cylinder,
    wherein the braking system is capable of affixing the respective positions of the first portion of the frame and the sled appendage in the first direction by the first brake cylinder extending the first extendable piston to push the first brake disc against the first stationary brake plate, and wherein the braking system is capable of affixing the respective positions of the first and second portions of the frame in the second direction by the second brake cylinder extending the second extendable piston to push the second brake disc against the second stationary brake plate.

9. The apparatus of claim 1, further comprising a transducer mounting supported by the frame and configured for supporting a plurality of transducers.

10. The apparatus of claim 1, further comprising:
a bubbler shoe supported by the frame and configured for supporting a plurality of transducers and dispersing a couplant between the transducers supported thereby and the surface over which the apparatus travels; and
a plurality of transducers supported by the bubbler shoe.

11. The apparatus of claim 10, wherein the bubbler shoe comprises:
a first layer;
a second layer disposed between the first layer and the surface over which the apparatus travels, wherein the first and second layers form an interior cavity; and
a fluid inlet for dispersing a couplant into the interior cavity;
wherein the first layer defines holes permitting wired connection to the transducers but configured to prevent the flow of the couplant through the holes; wherein the second layer defines holes through which the transducers extend toward the surface; and wherein the holes in the second layer are larger than transducers thereby permitting the couplant to pass around the transducers and through the second layer for individually coupling the transducers to the surface.

12. The apparatus of claim 11, wherein the first layer defines holes through which the transducers extend away from the surface providing access to the transducers for wired connection.

13. The apparatus of claim 1, wherein the sled appendage is configured with a longitudinal axis extending perpendicular to the first axis, with a surface side adjacent the surface of the structure over which the apparatus travels, and with the surface side of opposing distal ends of the longitudinal axis curved away from the surface.

14. The apparatus of claim 1, comprising a pair of sled appendages.

15. The apparatus of claim 1, wherein the frame is further configured for attachment to a motion control device for moving the apparatus over the structure for inspection.

16. A system for inspecting a structure, comprising:
a motion control system; and
a probe connected to and moved by the motion control system over the structure, the probe comprising:
at least one pulse echo ultrasonic transducer configured for inspecting the structure as the transducer is moved over the structure;
a frame configured for supporting the transducer;
at least one sled appendage extending beyond the frame and configured for supporting the frame while traveling over a surface of the structure and rotatably connected to the frame; and
a braking system in communication with the motion control system and capable of affixing the respective positions of the frame and sled appendage in at least a first direction of motion about a first axis defined by the rotatable connection of the frame and the sled appendage.

17. The system of claim 16, further comprising an extension coupler connected between the motion control system and the probe and configured for applying pressure to the probe for pressing the probe against the structure.

18. The system of claim 16, wherein the motion control system comprises electronic data representing the configuration of the structure, thereby providing the motion control system the ability to move the probe over the structure for inspection and the ability to communicate the location of holes and edges to the braking system.

19. The system of claim 16, wherein the motion control system is capable of providing a braking signal to the braking system of the probe based upon a determination of the location of the probe with respect to predetermined locations of holes and edges of the structure known to the motion control system.

20. A method for inspecting a structure, comprising the steps of:
providing a probe against a surface of the structure and connected to a motion control system, the probe comprises:
a frame for supporting at least one transducer;
at least one pulse echo ultrasonic transducer for transmitting and receiving pulse echo ultrasonic signals;
at least one sled appendage rotatably connected to the frame and for contacting the surface; and
an axial braking system for fixing the position of the sled appendage and in communication with the motion control system connected to the probe;
transmitting pulse echo ultrasonic signals from the transducer into the structure;
receiving pulse echo ultrasonic signals at the transducer reflected from the structure; and
temporarily fixing the position of the sled appendage for scanning a portion of the structure while only a portion of the probe is over the surface of the structure, wherein temporarily fixing the position of the sled appendage comprises the steps of:
transmitting a first signal for locking the position of the sled appendages;
receiving the first signal;
locking the position of the sled appendages;
transmitting a second signal for releasing the position of the sled appendages;
receiving the second signal; and
releasing the position of the sled appendages.

21. The method of claim 20, further comprising the step of coupling the pulse echo ultrasonic signals transmitted to and received from the structure using a couplant.

22. The method of claim 21, wherein the probe comprises a plurality of transducers each transmitting and receiving pulse echo ultrasonic signals, and wherein the step of coupling the pulse echo ultrasonic signals comprises dispersing a couplant to each transducer to individually couple the pulse echo ultrasonic signals transmitted therefrom and received thereby separate from the coupling of the other pulse echo signals transmitted from and received by the other transducers.

23. The method of claim 20, wherein the step of providing a probe against a surface of the structure comprises applying pressure to the probe to press the probe against the surface.

24. The method of claim 20, wherein the step of fixing the position of the sled appendage comprises activating the axial braking system.

25. The method of claim 20, wherein the sled appendage is rotatably connected to the frame about at least two axes thereby providing at least two directions of motion; and wherein the step of fixing the position of the sled appendage comprises fixing the respective position of the sled appendage in the at least two directions of motion by which the sled appendage is rotatably connected to the frame.

26. The method of claim 20, wherein the probe comprises at least two sled appendages; wherein the sled appendage are rotatably connected to the frame about at least one axis thereby providing at least one direction of motion; and wherein the step of fixing the position of the sled appendages comprises individually fixing the respective positions of the sled appendages in at least one direction of motion by which the sled appendages are rotatably connected to the frame.

* * * * *